(12) United States Patent
Kajimoto et al.

(10) Patent No.: US 6,566,346 B2
(45) Date of Patent: May 20, 2003

(54) ORAL SKIN IMPROVING AGENT, SKIN IMPROVING METHOD, AND FOOD COMPOSITION FOR IMPROVING SKIN

(75) Inventors: Osami Kajimoto, Osaka (JP); Wakako Sakamoto, Tokyo (JP); Wataru Odanaka, Tokyo (JP); Kazuya Yoshida, Tokyo (JP)

(73) Assignee: Q.P. Corporation, Tokyo (JP)

( * ) Notice: Subject to any disclaimer, the term of this patent is extended or adjusted under 35 U.S.C. 154(b) by 0 days.

(21) Appl. No.: 10/093,388

(22) Filed: Mar. 11, 2002

(65) Prior Publication Data

US 2003/0050277 A1 Mar. 13, 2003

(30) Foreign Application Priority Data

Mar. 27, 2001 (JP) ........................................ 2001-089187
Jul. 30, 2001 (JP) ........................................ 2001-229808

(51) Int. Cl.[7] .................... A01N 43/04; A61K 31/715; A61K 31/70; C07H 5/04; C07H 5/06
(52) U.S. Cl. .................... 514/54; 514/62; 514/420; 514/427; 514/560; 536/55.1; 536/55.2; 536/55.3; 424/476
(58) Field of Search ............................ 514/54, 62, 420, 514/427, 560; 536/55.1, 55.2, 55.3; 424/476

(56) References Cited

U.S. PATENT DOCUMENTS 4,141,973 A * 2/1979 Balazs et al.
5,811,410 A * 9/1998 Falk et al.

FOREIGN PATENT DOCUMENTS

| CN | 1285193 | * | 2/2001 |
|---|---|---|---|
| JP | 61-47418 | | 3/1986 |
| JP | 62-224268 | | 10/1987 |
| JP | 5-111367 | | 5/1993 |
| JP | 10-165138 | | 6/1998 |
| JP | 11-308977 | | 11/1999 |
| JP | 2000-102362 | | 4/2000 |

OTHER PUBLICATIONS

Chapter 1, pp. 46–49, "General Components And Related Components", 1–4; Fats, 1–4–2: Ether Extraction Method in 'Shin–Shokuhin–Bunseki–ho' ('New Food Analysis Methods'), Published by Korin Publishing Co., Ltd.

* cited by examiner

Primary Examiner—James O. Wilson
Assistant Examiner—Traviss C. McIntosh
(74) Attorney, Agent, or Firm—Oblon, Spivak, McClelland, Maier & Neustadt, P.C.

(57) ABSTRACT

There are provided an oral skin improving agent that exhibits good skin improving effects when orally ingested, suppresses problems of discoloration and generation of unpleasant odor during storage, and has excellent storage stability; a food composition for improving skin containing this skin improving agent; and a skin improving method. The oral skin improving agent contains as a principal component refined hyaluronic acid having a purity of at least 90%, preferably at least 95%, and an average molecular weight in a range of 750,000 to 1,200,000, preferably 800,000 to 1,000,000. A person's skin can be improved by having the person ingest the oral skin improving agent such that the ingestion amount thereof is at least 5 mg per day.

11 Claims, No Drawings

ORAL SKIN IMPROVING AGENT, SKIN IMPROVING METHOD, AND FOOD COMPOSITION FOR IMPROVING SKIN

BACKGROUND OF THE INVENTION

1. Field of the Invention

The present invention relates to an oral skin improving agent to be orally administered or ingested, a skin improving method and a food composition for improving skin, for improving the skin condition of humans.

2. Description of the Related Art

Hyaluronic acid, which is classified as a polysaccharide having as constituent repeating units the two saccharides, glucuronic acid and N-acetylglucosamine, is a high molecular weight substance that is synthesized in the body, has an extremely high water holding capacity, and is known to play an important role in the elasticity and suppleness of the skin (particularly the corium).

The amount of hyaluronic acid in skin cells decreases with age, and accompanying this the elasticity and suppleness of the skin drop, and skin roughness and fine wrinkles appear.

Hitherto, hyaluronic acid has thus been blended as a moisturizing agent into cosmetics that are applied to the skin, in the expectation that skin moistness will be maintained and skin roughness improved.

However, human skin has inherently a function of protecting the body from external factors, i.e., a biological defense function, and hence it is thought that it is difficult for hyaluronic acid of high molecular weight to pass through the epidermis and reach the corium. Hyaluronic-acid-containing cosmetics thus predominantly utilize the moisturizing effect produced when hyaluronic acid is applied to the skin, and hence the current state of affairs is that an essential effect for improving skin roughness in which the hyaluronic acid acts right inside the skin is not obtained.

It has thus been proposed that hyaluronic acid be put into the body not via the skin but rather by oral ingestion. For example, a foodstuff containing hyaluronic acid and a protein made into peptide form through enzymatic degradation with a protease (Japanese Patent Application Laid-open No. H5-111367 (U.S. Pat. No. 2,787,254)), and a food additive that contains hyaluronic acid of average molecular weight 10,000 to 500,000 and for which the intestinal absorption of the hyaluronic acid is improved (Japanese Patent Application Laid-open No. 2000-102362 etc.), have been proposed.

However, in the case of the hyaluronic acid used in the foodstuff disclosed in Japanese Patent Application Laid-open No. H5-111367, according to the manufacturing method thereof (Examples (paragraphs 0006, 0007)), peptides are intentionally included therein, and hence the degree of refining and the purity of the hyaluronic acid are low. There is thus a problem that, if this foodstuff is used as a food or a food ingredient as is, then discoloration and generation of an unpleasant odor will occur during storage of the food.

Moreover, the hyaluronic acid used in the food additive disclosed in Japanese Patent Application Laid-open No. 2000-102362 is again not high-purity hyaluronic acid as used in cosmetics, but rather cheap unrefined hyaluronic acid intended for use in foods. There is thus a problem that, as above, when this unrefined hyaluronic acid is used, discoloration and generation of an unpleasant odor occur during storage. Moreover, even if refining were carried out, there is still a problem in that skin improving effects as good as those hoped for will not be obtained with hyaluronic acid having an average molecular weight in a range of 10,000 to 500,000.

SUMMARY OF THE INVENTION

An object of the present invention is to provide an oral skin improving agent that has hyaluronic acid as a principal component, that exhibits good skin improving effects when orally ingested, and for which the problems of discoloration and generation of an unpleasant odor during storage are suppressed; a food composition for improving skin containing this skin improving agent; and a skin improving method.

The present inventors perfected the present invention after discovering that the above object can be achieved if refined hyaluronic acid having a purity of at least a certain specified value and an average molecular weight within a certain specified range is used as the hyaluronic acid.

Specifically, the present invention provides an oral skin improving agent that comprises hyaluronic acid having a purity of at least 90% and an average molecular weight in a range of 750,000 to 1,200,000.

The present invention also provides a method of improving human skin that comprises the step of having a human ingest the above-mentioned oral skin improving agent, such that the ingestion amount of the hyaluronic acid having a purity of at least 90% and an average molecular weight in a range of 750,000 to 1,200,000 is at least 5 mg per day.

Moreover, the present invention also provides a food composition for improving skin that comprises the above-mentioned oral skin improving agent.

DESCRIPTION OF THE PREFERRED EMBODIMENTS

Following is a detailed description of the present invention. Note that unless otherwise stated, '%' in this description means 'mass %'.

The oral skin improving agent of the present invention uses refined hyaluronic acid having a low impurity content, specifically having a purity of at least 90%, preferably at least 95%, and moreover having an average molecular weight in a range of 750,000 to 1,200,000, preferably 800,000 to 1,000,000. It is undesirable for the purity to be less than 90%, since then discoloration will occur during storage and hence the appearance will be impaired, and moreover an unpleasant odor will be generated. Moreover, it is undesirable for the hyaluronic acid to have an average molecular weight outside the range of 750,000 to 1,200,000, since it may not be possible to obtain sufficient skin improving effects when such hyaluronic acid is ingested. The exact reason for this is unclear, but it is thought that when products of the decomposition (resolvents deriving from hyaluronic acid) in the digestive organs of hyaluronic acid having an average molecular weight within the above-mentioned range are absorbed from the intestines and the like, hyaluronic acid synthesis in the corium is promoted.

The refined hyaluronic acid used in the present invention can come from any of various raw materials. Examples of such raw materials include biological tissue containing hyaluronic acid such as chickencomb, umbilical cord, eyeball, skin and cartilage, and culture solutions obtained by culturing hyaluronic-acid-producing microorganisms such as microorganisms of the Streptococcus genus.

As stated above, the purity of the refined hyaluronic acid used in the present invention is at least 90%. Here, the purity is defined as the value obtained by subtracting the amount of impurities, i.e. things other than hyaluronic acid, from 100% in terms of dry matter. Examples of such impurities include protein decomposition products, fatty substances (crude fat), and chondroitin sulfate. Specifically, the purity of refined hyaluronic acid obtained from chickencomb as a raw material can be calculated from Equation (1) below.

[Purity of hyaluronic acid (%)]=100−[protein decomposition products (%)]−[crude fat (%)]−[chondroitin sulfate (%)]  (1)

In Equation (1), the amount of protein decomposition products (%) is determined by the Lowry method, the amount of crude fat (%) is determined as described in 'Chapter 1: General Components and Related Components, 1-4: Fats, 1-4-2: Ether Extraction Method' in 'Shin-shokuhin-bunseki-ho' ('New Food Analysis Methods') (published by Korin Publishing Co., Ltd.), and the amount of chondroitin sulfate (%) is obtained through the method described below.

To determine the amount of chondroitin sulfate, firstly, the refined hyaluronic acid is dried, 50 mg thereof is weighed out accurately, and then the refined hyaluronic acid is dissolved by adding purified water and is made up accurately to 100 ml, thus obtaining a test solution. 4 ml of the test solution is put into a test tube, 1 ml of sulfuric acid of concentration 0.5 mol/l is added and mixing is carried out, and the mixture is then heated in a water bath for 10 minutes and then cooled. 0.2 ml of cetyltrimethylammonium bromide of concentration 0.04 mol/l is added to the cooled solution and mixing is carried out, the mixture is left at room temperature for 1 hour, and then the absorbance of light of wavelength 660 nm, using a measuring cell of a 10 mm-length, is measured.

Next, the amount of chondroitin sulfate (%) in the refined hyaluronic acid is determined from the absorbance data using a chondroitin sulfate calibration curve. The calibration curve is obtained as follows. Chondroitin sulfate A sodium salt obtained from whale cartilage (SG (special grade), made by Seikagaku Corporation) is dried (reduced pressure, phosphorus pentoxide, 60° C., 5 hours) and weighed out accurately, and then purified water is added to dissolve the chondroitin sulfate A sodium salt. In this way, solutions containing 10 μg, 20 μg, 30 μg and 40 μg of chondroitin sulfate A sodium salt per ml are prepared. For each of the solutions, 1 ml of sulfuric acid of concentration 0.5 mol/l is added to 4 ml of the solution and mixing is carried out, and then 0.2 ml of cetyltrimethylammonium bromide of concentration 0.04 mol/l is added and mixing is carried out, the mixture is left at room temperature for 1 hour, and then the absorbance of light is measured as above. The absorbance (vertical axis) is plotted against the chondroitin sulfate A sodium salt solution concentration (μg/ml) (horizontal axis), thus obtaining the calibration curve.

The average molecular weight of the refined hyaluronic acid used in the present invention is defined as the value determined through the following method.

About 0.05 g of the refined hyaluronic acid is weighed out accurately, and is then dissolved in sodium chloride solution of concentration 0.2 mol/l and made up accurately to 100 ml. 8 ml, 12 ml and 16 ml of the resulting solution are measured out accurately, and sodium chloride solution of concentration 0.2 mol/l is added to each to make up accurately to 20 ml, thus obtaining sample solutions. The specific viscosity of each of the sample solutions and also of the sodium chloride solution of concentration 0.2 mol/l is measured at 30.0±0.1° C. in accordance with 'General Test Methods, Viscosity Measurement Methods, Method 1: Capillary Tube Viscosity Measurement Method' in the Japanese Pharmacopoeia (13$^{th}$ Revision) (Equation (2)), and then the reduced viscosity for each concentration is calculated (Equation (3)). The reduced viscosity (vertical axis) is then plotted against the concentration in terms of a dry form of refined hyaluronic acid (g/100 ml) (horizontal axis), the plotted points are joined together by a straight line, and the intrinsic viscosity is obtained as the point where this straight line intersects the vertical axis. The intrinsic viscosity thus obtained is substituted into Laurent's formula (Equation (4)), thus calculating the average molecular weight.

[Specific viscosity]={[Time required to flow down for sample solution]/[Time required to flow down for 0.2 mol/l sodium chloride solution]}−1  (2)

[Reduced viscosity]=[Specific viscosity]/[Concentration in terms of a dry form of refined hyaluronic acid (g/100 ml)]  (3)

(Intrinsic viscosity)=$3.6 \times 10^{-4} M^{0.78}$  (4)

M: Average molecular weight (Daltons)

The refined hyaluronic acid described above can be manufactured following a publicly known hyaluronic acid manufacturing method in accordance with the type of raw material used and the like, with the proviso that the purity of the hyaluronic acid is at least 90% and the average molecular weight is in a range of 750,000 to 1,200,000. A description will now be given of a preferable manufacturing method for the case that the raw material is chickencomb, which is cheap and easy to obtain.

Firstly, the chickencomb is subjected to heat treatment. This is to thermally denature proteins contained in the chickencomb and deactivate enzymes. Any method may be used for the heat treatment, but the heat treatment can be carried out efficiently by immersing the chickencomb in hot water. There are no particular limitations on the heating temperature and time, provided that this temperature and time are within a range such that proteins are thermally denatured and enzymes deactivated. In the case that the heat treatment is carried out using hot water, the chickencomb is preferably immersed in hot water of temperature 60 to 100° C. for 20 to 90 minutes.

Note that if frozen chickencomb is used, then although the frozen chickencomb may be heated as is, it is preferable to carry out the heat treatment after the frozen chickencomb has been thawed slowly, for example by placing under running water, since it will then be easier to obtain a constant product quality.

Next, the chickencomb that has been subjected to the heat treatment is made into a paste. By making the chickencomb into a paste, the hyaluronic acid yield can be increased. Before making into a paste, if the chickencomb is shredded using a shredder, a minced meat chopper or the like after the heat treatment, then it becomes easier to make the chickencomb into a paste. An example of a method of making the chickencomb into a paste is to add about 1 to 5 times the amount of water to the chickencomb and then homogenize for 10 to 60 minutes in a homogenizer, whereupon a paste is produced. Alternatively, a high-speed agitator, a masher or the like may be used instead of the homogenizer.

Next, an acidic agent such as hydrochloric acid or sulfuric acid, or an alkaline agent such as sodium hydroxide or potassium hydroxide, is added to the chickencomb paste, thus carrying out acid treatment or alkali treatment, and hence reducing the molecular weight of the hyaluronic acid, such that the average molecular weight of the hyaluronic acid after refining will be in a range of 750,000 to 1,200,000, preferably 800,000 to 1,000,000. The molecular weight of the hyaluronic acid may be adjusted in this way by using a suitable combination of the concentration or amount added of the acidic agent or alkaline agent, the treatment time and so on, such that the molecular weight of the hyaluronic acid after the refining will be as desired. It is preferable to use alkali treatment, since it is easier to control the molecular weight of the hyaluronic acid in this case. An example of such alkali treatment for adjusting the molecular weight of the hyaluronic acid is to add about 1 to 5% of an alkaline aqueous solution of concentration 10 to 30% to the chickencomb paste and treat for about 15 to 90 minutes at 25 to 70° C., before neutralizing with hydrochloric acid or the like.

Next, protease treatment is carried out by adding a protease to the chickencomb for which the molecular weight of the hyaluronic acid has been adjusted. Any commercially available protease may be used, for example pepsin, trypsin, papain, bromelain or the like. It is appropriate for the amount added of the protease to be 0.01 to 1% relative to the amount of the chickencomb. Moreover, it is appropriate for the temperature and time of the protease treatment to be in the ranges 35 to 65° C. and 1 to 10 hours respectively.

Finally, hyaluronic acid is separated off from the protease-treated material, thus obtaining crude hyaluronic acid, and then this crude hyaluronic acid is refined, thus obtaining refined hyaluronic acid having a purity of at least 90% and an average molecular weight in a range of 750,000 to 1,200,000.

The separating off and refining of the hyaluronic acid can be carried out by conventional methods. For example, firstly, the protease-treated material is filtered to remove solid matter, thus obtaining a filtrate containing the crude hyaluronic acid. Note that before the filtration, the protease-treated material may be treated by adding activated charcoal, to deodorize and decolorize the material and also remove some of the protein decomposition products. Sodium chloride is next dissolved in the filtrate obtained, ethanol is added to precipitate the hyaluronic acid, and then the precipitate is separated off. Water-containing ethanol of ethanol concentration 80 to 95 vol % is then added to the precipitate, washing is carried out in a homogenizer, and the precipitate is separated off. This washing with water-containing ethanol of ethanol concentration 80 to 95 vol % is repeated about 2 to 10 times, and then the precipitate separated off is dried, thus obtaining the refined hyaluronic acid used in the present invention.

The oral skin improving agent of the present invention contains refined hyaluronic acid as described above. The hyaluronic acid content can be determined as appropriate in accordance with the dosage form of the oral skin improving agent. Moreover, the oral skin improving agent may consist of only the refined hyaluronic acid, with no other components added.

Publicly known additives (solvents, excipients etc.) may be blended into the oral skin improving agent of the present invention as required.

When the oral skin improving agent of the present invention is used in a skin improving method for humans, in order for the desired skin improving effects to be obtained, the amount ingested of the skin improving agent for an average adult (body weight about 60 kg) should preferably be such that the ingestion amount of the refined hyaluronic acid contained therein is at least 5 mg per day, more preferably at least 25 mg per day. However, if the refined hyaluronic acid ingestion amount is too high then effects commensurate with the ingestion will not be obtained, and hence the refined hyaluronic acid ingestion amount is preferably no more than 1500 mg per day, more preferably no more than 1000 mg per day. Here, 'skin improving effects' are the effects of maintaining the moistness of the skin and improving skin roughness, and maintaining the elasticity and suppleness of the skin.

A description will now be given of the food composition for improving skin of the present invention.

The food composition for improving skin of the present invention is a foodstuff that contains the oral skin improving agent of the present invention as described above, and is eaten to improve the skin. The form of the food composition for improving skin may be as the same as those of other general 'health foods', for example, tablets, capsules, granules or a liquid. However, considering the risk of the molecular weight of the hyaluronic acid dropping during storage and thus the skin improving effects being reduced, a dry form for which such dropping of the molecular weight is less prone to occur is preferable, for example tablets, capsules or granules.

The content of the oral skin improving agent in the food composition for improving skin may be set as appropriate based on the daily ingestion amount of the oral skin improving agent.

Various other foodstuff raw materials such as nutrients and excipients may be incorporated into the food composition of the present invention as appropriate, so long as this is within a range such that the effects of the present invention are not impaired. Examples thereof include various nutrients, for example vitamins such as vitamin C, vitamin B2, vitamin B12 and vitamin E, nutrients such as nucleic acids, chondroitin sulfate and collagen, minerals such as iron and zinc, and highly unsaturated fatty acids such as eicosapentaenoic acid and docosahexaenoic acid, and excipients, for example extenders, binders, lubricants, preservatives, antioxidants and aromatics.

The food composition for improving skin of the present invention must use as one raw material the oral skin improving agent comprising refined hyaluronic acid, but otherwise can be manufactured in accordance with conventional methods. For example, in the case of tablets, the tablets can be manufactured by weighing out the oral skin improving agent comprising refined hyaluronic acid along with other nutrients, excipients and the like, removing foreign matter if necessary using a sieve or the like, and then mixing all of the raw materials together uniformly using a mixer, and making the mixture thus obtained into tablets using a tablet machine.

EXAMPLES

Example 1 Oral skin improving agent (1) 3 kg of frozen chickencomb was thawed under running water, and then the chickencomb was heat treated in hot water at 80° C. for 40 minutes, and then cooled in water.

(2) 2 kg of the heat-treated chickencomb thus obtained was shredded in a cutting mixer (ROBOT-COUPE, made by TK FOOD MACHINERY, INC.), and then 4.21 of potable water was added, and the shredded chickencomb was homogenized into a paste using a homogenizer (PHYSCOTRON, made by NITI-ON).

(3) 52.5 g of 20% sodium hydroxide aqueous solution was added to the chickencomb that had been made into a paste, and alkali treatment to reduce the molecular weight of the hyaluronic acid was carried out at 55° C. for 1 hour, and then neutralized with hydrochloric acid.

(4) 1.0 g of a protease (Protease P 'Amano' 3, made by Amano Enzyme Inc.) was next added to the alkali-treated material, and protease treatment was carried out at 45° C. for 2 hours.

(5) 800 g of activated charcoal and 1.6 l of potable water were added to the protease-treated material, agitation was carried out for 1 hour, and then filtration was carried out using kieselguhr as a filter aid, and the filtrate was collected.

(6) Next, 700 g of sodium chloride was dissolved into the obtained filtrate with agitation, 5.4 l of ethanol was added to produce a precipitate, and once it had been confirmed that precipitate had formed sufficiently, the precipitate was separated off using a filter cloth.

(7) 0.5 l of water-containing ethanol of ethanol concentration 80 vol % was added to the obtained precipitate, and thorough washing was carried out in a homogenizer. After leaving to stand for a while, the precipitate was then separated off using a filter cloth. This procedure was repeated 4 times.

(8) Next, 0.5 l of water-containing ethanol of ethanol concentration 90 vol % was added to the precipitate, and washing was carried out a further 2 times as in step (7) above.

(9) The precipitate was dried for 10 hours at 50° C., thus obtaining an oral skin improving agent comprising a white powder, and gave off virtually no unpleasant odor. The purity of the refined hyaluronic acid was 96% according to Equation (1), and the average molecular weight was 980,000 according to Equations (2) to (4).

Comparative Example 1

Comparative Example of Oral Skin Improving Agent

The oral skin improving agent comprising hyaluronic acid of Comparative Example 1 was obtained by freeze-drying the filtrate obtained in step (5) in Example 1 above. The purity of this hyaluronic acid according to Equation (1) was 37%. The hyaluronic acid was an almost white powder, and gave off virtually no unpleasant odor.

Because the amount of impurities was high, the average molecular weight of this hyaluronic acid could not be determined from Equations (2) to (4). Nevertheless, it is thought that the average molecular weight should not change greatly during the refining steps, i.e., step (6) and following steps in Example 1, and thus that the average molecular weight of the hyaluronic acid obtained in Comparative Example 1 should be approximately the same as the average molecular weight of the refined hyaluronic acid of Example 1.

Example 2

Food Composition for Improving Skin

The raw materials listed in Table 1 were weighed out, and then sieved through a 16-mesh sieve. The raw materials were next put into a mixer, and thoroughly mixed into a uniform mixture, and then tablets each of weight about 240 mg were made using a tablet machine, thus obtaining a tablet type food composition for improving skin.

TABLE 1

| Component | Wt % |
| --- | --- |
| Oral skin improving agent (obtained in Example 1) | 25 |
| Lactose | 24 |
| Crystalline cellulose | 20 |

TABLE 1-continued

| Component | Wt % |
| --- | --- |
| Cornstarch | 15 |
| Dextrin | 10 |
| Glycerine fatty acid ester | 5 |
| Silicon dioxide | 1 |
| Total | 100% |

Comparative Example 2

Comparative Example of Food Composition for Improving Skin

A food composition for improving skin for the purpose of comparison was obtained using the same procedure as in Example 2, only using the raw materials listed in Table 2.

TABLE 2

| Component | Wt % |
| --- | --- |
| Lactose | 49 |
| Crystalline cellulose | 20 |
| Cornstarch | 15 |
| Dextrin | 10 |
| Glycerine fatty acid ester | 5 |
| Silicon dioxide | 1 |
| Total | 100% |

EVALUATION

Evaluation Test Example 1

The oral skin improving agents of Example 1 and Comparative Example 1 were each stored at 40° C. for 3 weeks, and then evaluation was carried out regarding discoloration and unpleasant odor after the storage. The results obtained are shown in Table 3.

TABLE 3

| | Purity of hyaluronic acid | Discoloration and unpleasant odor after storage |
| --- | --- | --- |
| Example 1 | 96% | Almost white, no unpleasant odor |
| Comparative Example 1 | 37% | Clearly discolored, unpleasant odor noticed |

As shown in Table 3, the oral skin improving agent of Example 1 for which the purity of the hyaluronic acid was above 90% had excellent storage stability, with discoloration and generation of an unpleasant odor not being prone to occur.

Evaluation Test Example 2

The following test was carried out to verify that the food composition for improving skin containing the oral skin improving agent of the present invention has excellent skin improving effects.

22 people (3 men and 19 women, average age 26.7±6.6 years) who had chronically dry skin and were troubled by skin roughness were taken as test subjects (for all of these people, the moisture content on the inside of the left upper arm was found to be less than 50% in a skin moisture content test). The test subjects were divided into 2 groups, and after a 2-week observation period, the test subjects were made to ingest 2 tablets each morning and evening for 6 weeks, with the test subjects of one group ingesting the tablet-type food composition for improving skin of Example 2, and the test subjects of the other group ingesting the tablet-type food composition for improving skin of Comparative Example 2. The state of the test subjects' skin before and after the ingestion period was evaluated through (1) a dermatological examination, (2) a moisture content test, and (3) analysis using a microscopic skin surface analyzer (Visioscan), as described below. The tests were carried out as a double blind study. The values given in the tables below are mean values, and the results before and after the ingestion period were statistically analyzed using a Wilcoxon test.

(1) Dermatological Examination

The same dermatologist examined for the two symptoms, dryness and flush, on the face of each of the test subjects, and evaluated each symptom using a 4-level scoring system as below. The results obtained are shown in Table 4.

Scoring System

0: Symptom not present
1: mild
2: Moderate
3: Severe

TABLE 4

| Symptom | Food composition | Number of subjects with symptom | Before control period | Before intake period | 6-week after intake |
|---|---|---|---|---|---|
| Dryness | Example 2 | 11 | 2.3 | 2.4 | 1.0* |
| | Comparative Example 2 | 11 | 2.0 | 2.1 | 1.6 |
| flush | Example 2 | 9 | 2.0 | 2.0 | 0.9* |
| | Comparative Example 2 | 6 | 2.0 | 2.0 | 1.5 |

*P < 0.01

(2) Moisture Content

The moisture content at a point 1 cm under the left eye was measured using a moisture measuring device (Corneometer CM825, made by Courage+Khazaka Electronic GmbH).

To make the measurement conditions as near as possible the same in every case, a meeting room with the conditions set to be in a fixed range (room temperature 20.5 to 23.5° C., humidity 45 to 60%) was prepared, and each test subject was made to wait in a resting state in the meeting room for at least 30 minutes before the examination. Moreover, the test subjects were forbidden in principle from wearing makeup on the part of the face where the measurement would be taken from 60 minutes before the examination. Anyone who arrived wearing makeup was made to remove their makeup during the period of waiting in a resting state, and then the examination was carried out after at least 60 minutes had elapsed. The results obtained are shown in Table 5.

TABLE 5

| Food composition | Number of test subjects | Before control period | Before intake period | 6-week after intake |
|---|---|---|---|---|
| Example 2 | 11 | 45.7 ± 7.9% | 45.6 ± 7.5% | 51.9 ± 9.5%** |
| Comparative Example 2 | 11 | 45.7 ± 8.9% | 45.8 ± 12.0% | 47.9 ± 15.5% |

**P < 0.1

(3) Analysis using Microscopic Skin Surface Analyzer Visioscan

The smoothness (kurtosis) of the skin as a whole on the back of the neck was analyzed using a microscopic skin surface analyzer (Visioscan, made by Courage+Khazaka Electronic GmbH)

This analysis was carried out as follows. The 15 mm×17 mm rectangle surface of the skin was irradiated with an ultraviolet light, an image thereof was captured using a high-performance CCD camera, conversion to an 8-bit digital image was carried out on a personal computer, with the hue at each point in the image being represented by one of 256 gray scale values, and then the smoothness (kurtosis) of the skin as a whole was analyzed based on the nature of the histogram of these hue values over the image. The closer the value obtained as a result of the analysis is to 0, the smoother the curve of the histogram of the hue values, and hence the closer the skin is to being ideal. The results obtained are shown in Table 6.

TABLE 6

| Food composition | Number of test subjects | Before control period | Before intake period | 6-week after intake |
|---|---|---|---|---|
| Example 2 | 11 | 0.47 ± 0.08 | 0.50 ± 0.11 | 0.38 ± 0.09*** |
| Comparative Example 2 | 11 | 0.41 ± 0.07 | 0.43 ± 0.05 | 0.38 ± 0.09% |

***P < 0.05

As can be seen from Table 4 (symptoms of dryness and flush on the face), Table 5 (moisture amount under left eye) and Table 6 (smoothness of skin as a whole on back of neck), for all of the evaluation results there is a statistically significant improvement after the ingestion period compared with before the ingestion period in the case of the food composition for improving skin of Example 2 containing the oral skin improving agent comprising hyaluronic acid, but no such statistically significant improvement in the case of the food composition for improving skin of Comparative Example 2.

It can be seen from the above results that the oral skin improving agent of the present invention and the food composition for improving skin containing the same exhibit excellent skin improving effects.

Example 3

To investigate the effect of the purity of the hyaluronic acid on discoloration and odor after storage of the oral skin improving agent, the following 4 types of hyaluronic acid A to D were prepared as oral skin improving agents.

Hyaluronic acid A was the same as that manufactured in Example 1. The purity was thus 96%, and the average molecular weight 980,000.

Hyaluronic acid B was manufactured as in Example 1, only the alcohol washing was carried out only twice in step (7), and then the drying of step (9) was carried out (step (8) was not carried out). The purity of the hyaluronic acid was 90%, and as in Example 1 the average molecular weight calculated from Equations (2) to (4) was 980,000.

Hyaluronic acid C was manufactured as in Example 1 up to step (6), and then the drying of step (9) was carried out on the precipitate obtained after step (6) (steps (7) and (8) were not carried out). The purity of the hyaluronic acid was 83%. Because the amount of impurities was high, the average molecular weight could not be calculated from Equations (2) to (4); nevertheless, it is thought that the average molecular weight should not change greatly during the refining steps, and thus that the average molecular weight should be about the same as that of hyaluronic acid A.

Hyaluronic acid D was the same as that manufactured in Comparative Example 1. The purity was thus 37%. Again, because the amount of impurities was high, the average molecular weight could not be calculated from Equations (2) to (4); nevertheless, it is thought that the average molecular weight should not change greatly during the refining steps, and thus that the average molecular weight should be about the same as that of hyaluronic acid A.

The oral skin improving agents comprising hyaluronic acids A to D were each stored at 40° C. for 3 weeks, and then the discoloration and odor after the storage were evaluated in accordance with the following evaluation criteria, and an overall judgement was made. The results obtained are shown in Table 7.

Discoloration Evaluation Criteria

Rank: State
A: White—no discoloration
B: Slight discoloration
C: Considerable discoloration Odor Evaluation Criteria Rank: State
A: No unpleasant odor
B: Slight unpleasant odor
C: Considerable unpleasant odor Overall Judgement Rank Criteria
AA: Discoloration and odor evaluations both 'A'
A: One of discoloration and odor evaluations 'A', other 'B'
B: Discoloration and odor evaluations both 'B'
C: At least one of discoloration and odor evaluations 'C'

TABLE 7

| Hyaluronic acid | Purity (%) | Average molecular weight | Discoloration | Odor | Overall judgement |
|---|---|---|---|---|---|
| A | 96 | 980,000 | A | A | AA |
| B | 90 | 980,000 | A | B | A |
| C | 83 | (980,000) | B | B | B |
| D | 37 | (980,000) | C | C | C |

It can be seen from the results in Table 7 that for the hyaluronic acid to have good storability, the purity should be at least 90%, preferably at least 95%.

Example 4

To investigate the effect of the average molecular weight of the hyaluronic acid on the skin improving effects of the oral skin improving agent, the following 5 types of hyaluronic acid E to I were prepared as oral skin improving agents.

Hyaluronic acid E was the same as that manufactured in Example 1. The average molecular weight was thus 980,000, and the purity 96%.

Hyaluronic acids F to I were manufactured as in Example 1, only the alkali treatment time in step (3) was changed to 90 minutes, 40 minutes, 100 minutes and 20 minutes respectively (with the other conditions of the alkali treatment being left unchanged), resulting in the average molecular weights being 780,000, 1,150,000, 710,000 and 1,270,000 respectively. In all cases, the same refining conditions were used as in Example 1, and hence the purity was about the same as that of hyaluronic acid E.

A panel test was carried out on each of the oral skin improving agents comprising hyaluronic acids E to I, using 50 women (average age 28 years) who had chronically dry skin and were troubled by skin roughness as test subjects.

Firstly, a pre-test questionnaire was conducted to verify the state of the skin of each of the test subjects, and then based on the results of the pre-test questionnaire the 50 test subjects were divided into 5 groups each of 10 people in such a way that there was no imbalance in the state of the skin of the test subjects between the groups. The test subjects in each group were made to ingest 2 tablets of a tablet type oral skin improving agent prepared as in Example 2 each morning and evening for 3 weeks, and then a questionnaire survey was conducted regarding the state of the skin before and after the ingestion period. In the questionnaire survey, the test subjects were asked to rank the state of their skin in accordance with the following evaluation criteria. The results obtained are shown in Table 8.

Skin State Evaluation Criteria

Rank: Skin state
A: Greatly improved
B: Improved
C: Slightly improved
D: No change noticed

TABLE 8

| Hyaluronic acid | Average molecular weight | Number of test subjects | Skin state (number of persons) | | | |
|---|---|---|---|---|---|---|
| | | | A | B | C | D |
| E | 980,000 | 10 | 2 | 7 | 1 | 0 |
| F | 780,000 | 10 | 1 | 3 | 5 | 1 |
| G | 1,150,000 | 10 | 0 | 4 | 4 | 2 |
| H | 710,000 | 10 | 0 | 0 | 3 | 7 |
| I | 1,270,000 | 10 | 0 | 0 | 1 | 9 |

It can be seen from Table 8 that for the hyaluronic acid to have good skin improving effects, the average molecular weight of the hyaluronic acid should be in a range of 750,000 to 1,200,000, preferably 800,000 to 1,000,000.

The oral skin improving agent of the present invention and the food composition for improving skin containing the same exhibit good skin improving effects upon oral ingestion, and moreover have excellent storage stability, with the problems of discoloration and generation of an unpleasant odor during storage being suppressed.

The entire disclosure of the specifications, summaries, claims and abstracts of Japanese Patent Application Nos. 2001-89187 and 2001-229808 filed on Mar. 27, 2001 and Jul. 30, 2001, respectively, are hereby incorporated by reference.

What is claimed is:

1. An oral administratable agent for at least one purpose of maintaining moistness, improving roughness, maintaining elasticity or maintaining suppleness of the skin of a human, comprising hyaluronic acid having a purity of at least 90% and an average molecular weight in a range of 750,000 to 1,200,000 Daltons.

2. The agent according to claim 1, wherein the purity of said hyaluronic acid is at least 95%.

3. The agent according to claim 1, wherein the average molecular weight of said hyaluronic acid is in a range of 800,000 to 1,000,000 Daltons.

4. A method for at least one purpose of maintaining moistness, improving roughness, maintaining elasticity or maintaining suppleness of human skin, comprising orally administering to a human the agent according to claim 1, in an amount of at least 5 mg per day.

5. A food composition comprising the agent according to claim 1.

6. The agent according to claim 2, wherein the average molecular weight of said hyaluronic acid is in a range of 800,000 to 1,000,000 Daltons.

7. The method according to claim 4, wherein said hyaluronic acid has a purity of at least 95%.

8. The method according to claim 4, wherein said hyaluronic acid has an average molecular weight in a range of 800,000 to 1,000,000 Daltons.

9. The method according to claim 7, wherein said hyaluronic acid has an average molecular weight in a range of 800,000 to 1,000,000 Daltons.

10. A food composition comprising the agent according to claim 2.

11. A food composition comprising the agent according to claim 3.

* * * * *